United States Patent
Klemarczyk et al.

(10) Patent No.: US 8,729,179 B1
(45) Date of Patent: May 20, 2014

(54) MOISTURE CURABLE POLYACRYLATES

(71) Applicants: Philip T. Klemarczyk, Canton, CT (US); Anthony F. Jacobine, Meriden, CT (US); Joel D. Schall, Hamden, CT (US)

(72) Inventors: Philip T. Klemarczyk, Canton, CT (US); Anthony F. Jacobine, Meriden, CT (US); Joel D. Schall, Hamden, CT (US)

(73) Assignee: Henkel US IP LLC, Rocky Hill, CT (US)

( * ) Notice: Subject to any disclaimer, the term of this patent is extended or adjusted under 35 U.S.C. 154(b) by 0 days.

(21) Appl. No.: 13/738,348

(22) Filed: Jan. 10, 2013

Related U.S. Application Data

(60) Provisional application No. 61/684,829, filed on Aug. 20, 2012.

(51) Int. Cl.
| | |
|---|---|
| C08L 57/10 | (2006.01) |
| C07F 7/02 | (2006.01) |
| C07F 7/08 | (2006.01) |

(52) U.S. Cl.
USPC ........... 524/588; 556/400; 556/413; 556/418; 556/436; 556/437

(58) Field of Classification Search
None
See application file for complete search history.

(56) References Cited

U.S. PATENT DOCUMENTS

| | | | | |
|---|---|---|---|---|
| 5,364,955 | A * | 11/1994 | Zwiener et al. | 556/418 |
| 5,986,014 | A | 11/1999 | Kusakabe et al. | |
| 6,274,688 | B1 | 8/2001 | Nakagawa et al. | |
| 6,420,492 | B1 | 7/2002 | Kusakabe et al. | |
| 7,323,519 | B2 * | 1/2008 | Kitano et al. | 525/331.9 |
| 7,388,038 | B2 | 6/2008 | Fujita et al. | |
| 2005/0234144 | A1* | 10/2005 | Bachon et al. | 521/137 |
| 2011/0166285 | A1* | 7/2011 | Zander et al. | 524/505 |
| 2012/0053296 | A1* | 3/2012 | Coffey et al. | 525/100 |

* cited by examiner

Primary Examiner — Robert S Loewe
(74) Attorney, Agent, or Firm — Steven C. Bauman

(57) ABSTRACT

A process for preparing moisture curable compounds and moisture curable compositions prepared from the product of that process is provided.

12 Claims, 3 Drawing Sheets

MOISTURE CURABLE POLYACRYLATES

BACKGROUND

1. Field

A process for preparing moisture curable compounds and moisture curable compositions prepared from the product of that process is provided.

2. Brief Description of Related Technology

Moisture curable monomers, oligomers and polymers, and compositions made therewith, are well-known and have been described extensively and used commercially for some time.

One such polymer is an alkoxysilane terminated polyacrylate. Commercially available moisture curable, alkoxysilane terminated polyacrylates (such as those available from Kaneka Corporation, Japan) are currently prepared in a two step process. See also U.S. Pat. Nos. 5,986,014, 6,274,688, and 6,420,492. In a disclosed process, bromine substitution with an unsaturated carboxylic acid is followed by hydrosilation with an alkoxysilane. This two step process can be expensive and time consuming for the manufacturer. In addition, the additional step increases operator handling, which may lead to a less pure product by for instance a greater chance of cross linking or the introduction of impurities. In the latter instance, further steps may be required in order to purify the product. An idealized form of the synthesis is shown below.

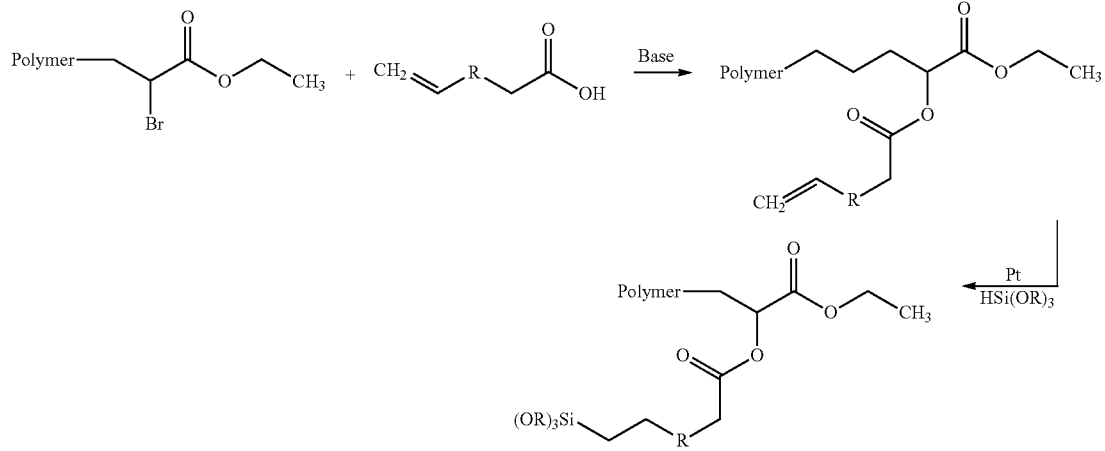

It would be desirable to identify alternative synthetic schemes by which to make such polymers for a variety of reasons, including raw material reactant availablity and reducing the complexity of the synthesis. For instance, reducing the number of synthetic steps can save on labor and time or processing, thereby creating a more efficient way in which to obtain these, and other, polymers.

SUMMARY

The present invention provides such a solution to that desire.

In one aspect a process for preparing aminoalkyl alkoxysilane-functionalized hydrocarbon compounds is provided. The process includes providing (a)

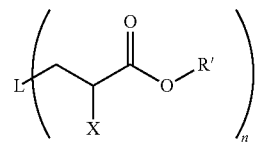

where L is alkyl or poly(alkyl), alkylene or poly(alkylene), alkenyl or poly(alkenyl), alkenylene or poly(alkenylene), aromatic or an aromatic ring system, X is a leaving group, R' is alkyl, and n is 1-4, or or

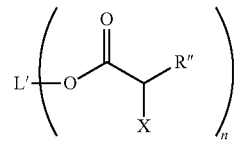

where L' is alkyl or poly(alkyl), alkylene or poly(alkylene), alkenyl or poly(alkenyl), alkenylene or poly(alkenylene), aromatic or an aromatic ring system, X is a leaving group, R" is alkyl, and n is 1-4, (b) an aminoalkylalkoxysilane, (c) base, and (d) organic solvent in a vessel and mixing (a)-(d) for a time sufficient to form an aminoalkyl alkoxysilane-functionalized hydrocarbon compound.

The present invention will be more fully appreciated by a reading of the "Detailed Description", and the illustrative examples which follow thereafter.

DETAILED DESCRIPTION

Figure 1:
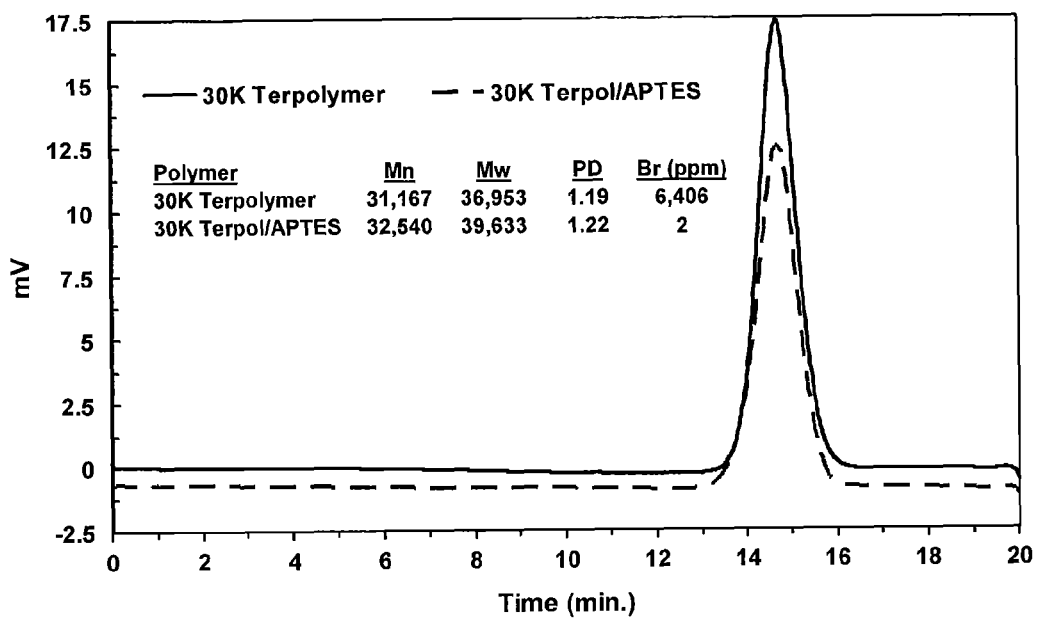
FIG. 1 shows GPC analysis of a 30,000 MW dibromobutyl-ethyl-methoxyethyl acrylate (75/20/5 mole ratio) terpolymer and the terpolymer/APTES product.

The present invention provides in one aspect a process for preparing an aminoalkylalkoxysilane-functionalized hydrocarbon compound made from (a)

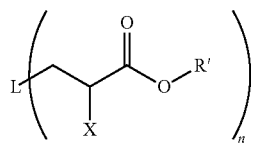

where L is alkyl or poly(alkyl), alkylene or poly(alkylene), alkenyl or poly(alkenyl), alkenylene or poly(alkenylene), aromatic or an aromatic ring system, X is a leaving group, R' is alkyl, and n is 1-4, or

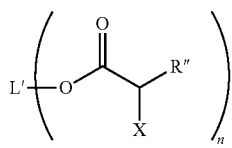

where L' is alkyl or poly(alkyl), alkylene or poly(alkylene), alkenyl or poly(alkenyl), alkenylene or poly(alkenylene), aromatic or an aromatic ring system, X is a leaving group, R" is alkyl, and n is 1-4, (b) an aminoalkylalkoxysilane, (c) base, and (d) organic solvent in a vessel and mixing (a)-(d) for a time sufficient to form an aminoalkylalkoxysilane-functionalized hydrocarbon compound.

L and L', or linker or linking groups, may be the same or different and are selected from alkyl or poly(alkyl), alkylene or poly(alkylene), alkenyl or poly(alkenyl), alkenylene or poly(alkenylene), aromatic or an aromatic ring system. The alkyl linker, when n is 1, may be an aliphatic group of 1 to 20 carbon atoms. The alkyl linker may be straight chain, branched chain or contain or be made from one or more cycloaliphatic group(s). The alkenyl linker, when n is 1, may be an unsaturated aliphatic group of 2 to 20 carbon atoms. The alkenyl linker may be straight chain, branched chain or contain or be made from one or more cycloaliphatic group(s). The aromatic linker, when n is 1, may have 6 to 20 carbon atoms.

When n is 2-4, the alkylene linker may be straight chain, branched chain or contain or be made from one or more cycloaliphatic group(s) of 1 to 20 carbon atoms, as appropriate; the alkenylene linker may be straight chain, branched chain or contain or be made from one or more cycloaliphatic group(s) of 2 to 20 carbon atoms, as appropriate. The aromatic linker may have from 6 to 20 carbon atoms.

The polymer versions of the alkyl, alkylene, alkenyl and alkenylene groups are defined simililarly, except that each is made up of repeating residues in a block, graft or random order. The polymer versions are ordinarily defined by their molecular weights, which here are between about 1,000 Mn and about 50,000 Mn. A particularly desirable polymer version is a poly(acrylate) made from one or (meth)acrylate monomers.

The leaving group, X, is a halogen, tosylate or mesylate. Apart from fluorine, the halogens may be selected from chlorine, bromine or iodine. Desirably, the leaving group is a bromine.

R' and R" may be the same or different and may be selected from an alkyl group, as noted above, which may be from 1 to 10 carbon atoms, optionally interrupted by one or more oxygen atoms. Particularly desirable R' and R" groups are ethyl, propyl, butyl and hexyl, and methoxy ethyl.

The compound shown in structure I may be an alkyl 2-bromoalkanoate, such as an ethyl 2-bromoalkanoate, like an alkyl 2-bromohexanoate, advantageously ethyl 2-bromohexanoate or ethyl 2-bromoproprionate. The compound shown in structure II may be hexanediol di-2-bromohexanoate, as an example.

In one embodiment, the compound shown in structure I is a di-(2-bromoalkanoate, polyacrylate). See Example 3 infra for a representative structure thereof. Here, the di-(2-bromoalkanoate, polyacrylate) should have a molecular weight in the range of about 1,000 Mn to about 50,000 Mn, such as about 30,000 Mn.

The aminoalkylalkoxysilane may be chosen from a host of possible choices. For instance, the amino alkyl portion of the alkoxy silane may have as the alkyl residue a variety of linkages including methyl, ethyl, propyls, butyls, pentyls and hexyls, to name a few. The alkoxy portion of the alkoxysilane may be present once, twice or three times on the silicon atom of the silane and may be chosen from a variety of groups including methoxy, ethoxy, and propoxy.

A generic structure of the aminoalkylalkoxysilane may be seen below

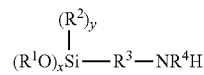

where $R^1$ and $R^2$ are selected from alkyl groups having from 1 to 4 carbon atoms, $R^3$ is selected from alkylene and arylene residues and $R^4$ is selected from hydrogen and alkyl groups having from 1 to 4 carbon atoms, and when x is 3, y is 0 and when x is 2, y is 1.

Examples of the aminoalkylalkoxysilanes include aminopropyltriethoxysilane ("APTES"), aminopropyltrimethoxysilane ("APTMS"), and aminopropyldiethoxymethylsilane ("APDEMS").

The aminoalkylalkoxysilane should be used in a molar excess to the compound shown in structures I or II. For instance, a 1.1 to 6 molar excess, such as 1.5 to 2.5 molar excess, is desirable.

In practicing the process, the base may be chosen from potassium carbonate or a trialkyl amine, such as diisopropyl ethylamine. The base is present in about an equimolar amount to the aminoalkylalkoxysilane.

The process is conducted in an organic solvent, which is polar and aprotic. Desirably, the organic solvent is acetonitrile.

In practicing the process, mixing occurs at ambient temperature followed by heating to reflux, such as at or around 83° C. for a reaction solvent containing acetonitrile. Reflux occurs for a period of time of about 2 to about 24 hours. Mixing at reflux desirably occurs for a period of time of about 2 to about 24 hours to achieve a yield of greater than about 90% of the aminoalkylalkoxysilane-functionalized hydrocarbon compound.

The process for preparing the aminoalkylalkoxysilane-functionalized hydrocarbon compounds from

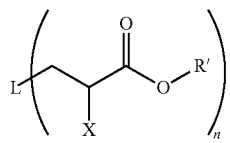

where L is alkyl or poly(alkyl), alkylene or poly(alkylene), alkenyl or poly(alkenyl), alkenylene or poly(alkenylene), aromatic or an aromatic ring system, X is a leaving group, R' is alkyl, and n is 1-4 or

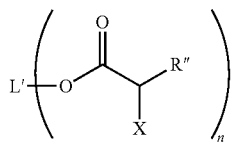

where L' is alkyl or poly(alkyl), alkylene or poly(alkylene), alkenyl or poly(alkenyl), alkenylene or poly(alkenylene), aromatic or an aromatic ring system, X is a leaving group, R" is alkyl, and n is 1-4, may employ a compound having a polymeric, oligomeric or elastomeric central portion for L and L', as noted above. In such a situation, it may be particlarly useful to engage a controlled radical polymerization, which is capable of introducing a given functional group into a defined position on the polymer, such as at the terminus. The controlled radical polymerization is advantageous because of the low velocity polymerization and high tendency of termination by radical-radical coupling, a termination reaction does not easily take place, thus giving a polymer with a narrow molecular weight distribution (Mn/Mn=about 1.1 to 1.5), and because the molecular weight can be freely controlled by adjusting the monomer/initiator charge ratio.

A variety of controlled radical polymerization techniques may be used, including but not limited to atom transfer radical polymerization ("ATRP"), single electron transfer living radical polymerization ("SET-LRP")", and reversible addition fragment transfer ("RAFT"), to name a few. In ATRP a vinyl monomer is polymerized using an organohalogen compound or a sulfonyl halide compound as the initiator and a transition metal complex as the catalyst. In this method, which is particularly attractive in the context of the present invention, in addition to the noted advantages, a polymer having a halogen atom at its terminus may be formed. A halogen atom in that position on the polymer is particularly interesting because of the freedom offered for initiator and catalyst design. See e.g. U.S. Pat. No. 7,388,038.

In another aspect the product made by the inventive process may be formulated with a curable matrix. Desirably, the curable matrix comprises a moisture curable silicone, such as one bearing alkoxy functionality.

The moisture curable composition, whether formulated with a curable matrix or simply based on the aminoalkylalkoxysilane-functionalized hydrocarbon compounds made by the processes disclosed herein, should also include a moisture cure catalyst.

The moisture cure catalysts include tin IV salts of carboxylic acids, such as dibutyltin dilaurate, organotitanium compounds such as tetrabutyl titanate, and partially chelated derivatives of these salts with chelating agents such as acetoacetic acid esters and beta-diketones and amines. Desirably, tetraisopropyltitanate, dibutyltin dilaurate and tetramethylguandine at levels of 0.05-0.5% are used.

Other additives such as thickeners, non-reactive plasticizers, fillers, toughening agents (such as elastomers and rubbers) and other well-known additives may be incorporated therein where the art-skilled believes it would be desirable to do so. In addition, cross linking agents may also be incorporated therein, examples of which being substituted trialkoxysilanes, such as APTMS, APTES, APDEMS and vinyl trimethoxysilane.

The invention also provides a process for preparing a reaction product from the mositure curable composition, the steps of which include applying the composition to a desired substrate surface and exposing the composition to appropriate conditions for a time sufficient to cure the composition.

In view of the above description of the present invention, it is clear that a wide range of practical opportunities is provided. The following examples are provided for illustrative purposes only, and are not to be construed so as to limit in any way the teaching herein.

EXAMPLES

A. Synthesis

Ethyl 2-bromohexanoate ("EBH"), acetonitrile, diisopropyl ether, diisopropylethylamine, APTMS, APTES, basic alumina, and anhydrous potassium carbonate were purchased from the Aldrich Chemical company and were used as received.

$^1$H NMR and $^{13}$C NMR analyses were performed with CDCl$_3$ as solvent on a 300 MHz Varian NMR System. Infrared spectra were obtained on a Perkin Elmer Spectrum One FTIR Spectrometer equipped with a Universal ATR sampling accessory. Rheometry data was obtained on a TA Instruments AR2000EX Rheometer.

Example 1

EBH was treated with an aminopropylalkoxysilane, in the presence of a base [here, (i-Pr)$_2$N-Et)], in an acetonitrile solvent, along the lines shown in the reaction scheme below.

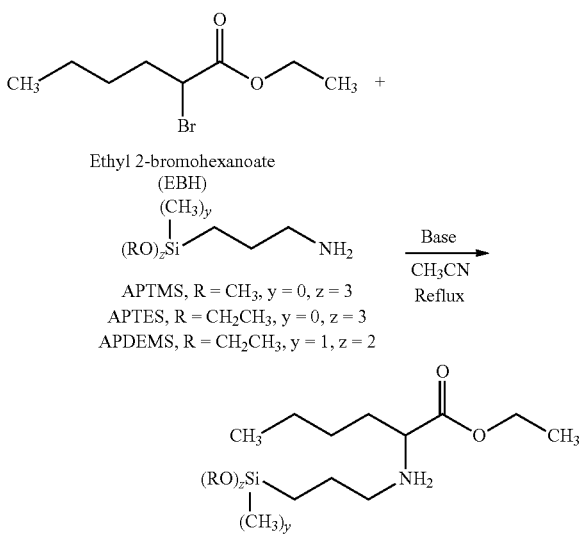

More specifically, and as shown in the reaction scheme below, to a 100 mL four-neck round bottom flask, equipped with a condenser, temperature controlling thermocouple, stir bar, magnetic stirrer, and a nitrogen inlet, is added ethyl 2-bromohexanoate (10 g, 45 mmol), APTMS (12.2 g, 67.5 mmol), (i-Pr)$_2$N-Et (8.7 g, 67.5 mmol), and (i-Pr)$_2$O (50 mL) under nitrogen. The reaction mixture was heated to reflux with stirring. After stirring overnight at reflux, it was then cooled to ambient temperature. The (i-Pr)$_2$N-Et hydrobromide salt precipitated from solution and was filtered. Solvent was removed under reduced pressure, and the product was vacuum dried. Yield=13.3 g (92%); $^1$H NMR (CDCl$_3$) δ 4.2 (q, 2, COOCH$_2$), 3.6 (s, 9, SiOCH$_3$), 3.2 (t, 1, NCH), 2.5 (m, 2, NCH$_2$), 1.6 (m, 4, CH$_2$), 1.3 (m, 4, CH$_2$), 1.2 (t, 3, COOCH$_2$CH$_3$), 0.9 (t, 3, CH$_3$), 0.7 (t, 2, SiCH$_2$); $^{13}$C NMR (CDCl$_3$) 175, 62, 60, 52, 51, 34, 28, 23.3, 22.7, 14.4, 13.9, 7; IR (neat) 2938, 1732, 1466, 1182, 1080, 1029, 812.

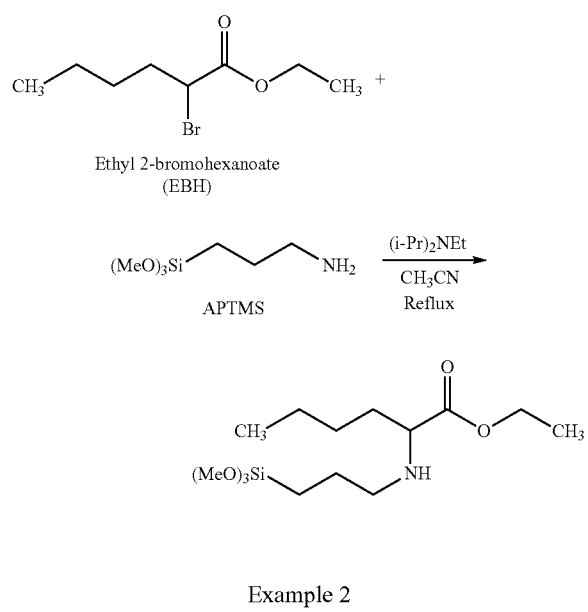

Example 2

Like Example 1, methoxyethyl 2-bromohexanoate ("MEBH") was treated with APTES under comparable conditions as described above.

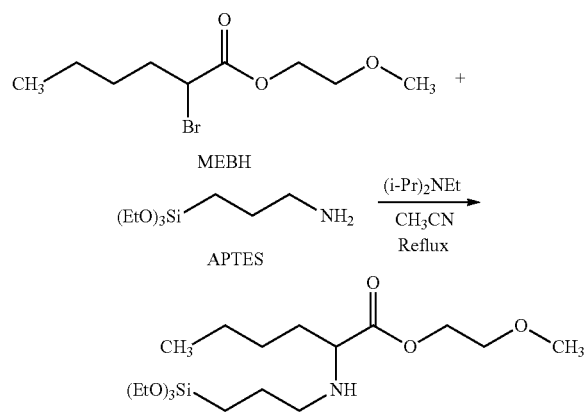

Example 3

A 30,000 Mn dibromo-terminated polybutyl acrylate prepared using atom transfer radical polymerization was then reacted with APTES, along the lines shown in the reaction scheme below.

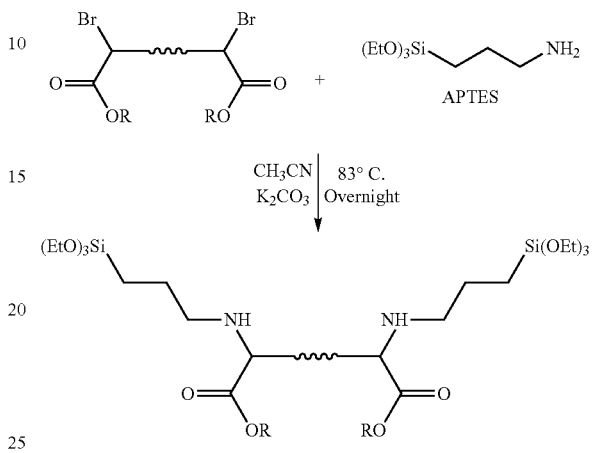

To a 250 mL four-neck round bottom flask, equipped with a condenser, temperature controlling thermocouple, stir bar, magnetic stirrer, and a nitrogen inlet, was added a 30,000 MW butyl-ethyl-methoxyethyl acrylate (75/20/5 mole ratio) terpolymer (20 g, 0.67 mmol), APTES (0.6 g, 2.7 mmol), potassium carbonate (0.4 g, 2.7 mmol), and acetonitrile (500 mL) under nitrogen. The reaction mixture was heated to reflux with stirring. After stirring overnight at reflux, it was then cooled to ambient temperature. Basic alumina (20 g) was added, and this mixture was stirred for about 4 hours and then filtered. Solvent was removed under reduced pressure, and the product was vacuum dried. Yield=14.1 g (72%); $^1$H NMR (CDCl$_3$) δ 4.0 (m), 3.8 (q), 3.6 (m), 3.4 (s), 2.3 (m), 1.9 (m), 1.6 (m), 1.4 (m), 1.2 (t), 0.9 (t), 0.6 (t); $^{13}$C NMR (CDCl$_3$) 175, 64, 61, 59, 41, 35, 31, 19, 14.2, 14, 4; IR (neat) 2959, 1728, 1449, 1243, 1157, 1063, 941, 842, 739.

A 14,000 Mn dibromo-polybutylacrylate was also prepared by atom transfer radical polymerization. This dibromo-polybutylacrylate was then reacted with APTES, as shown above.

Figure 2:
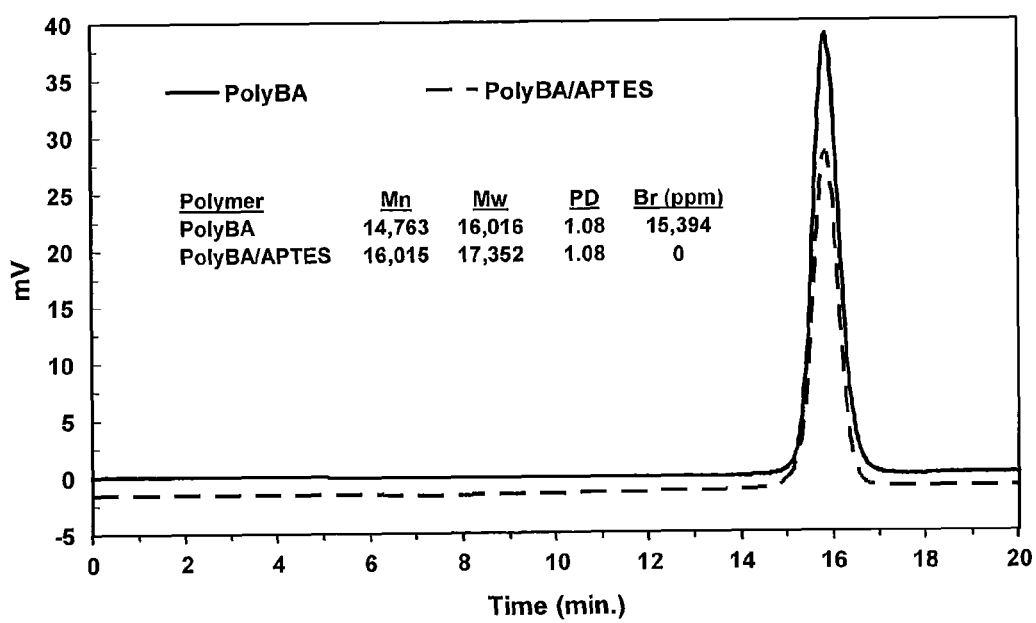
FIG. 2 shows GPC analysis of a 14,000 Mn dibromopolybutylacrylate (PolyBA) and the PolyBA/APTES product.

The resulting polymers were analyzed by gel phase chromatography ("GPC") to determine their molecular weight and polydispersity, and the GPC curves of the starting material and product, along with the GPC data, are shown in FIGS. 1 and 2.

B. Moisture Curable Adhesive Formulation

Each of the alkoxysilane adducts (termed in the table, "Experimental Resin"), MESAMOLL-brand plasticizer, and CAB-O-SIL TS530-brand silica were added to a mixing cup and were blended in a DAC 150 speedmixer. The two crosslinkers and the catalyst were then added, and the formulations mixed for a second time (both times for 3 minutes at 2750 rpm). Sample Nos. 1-4 were thus formed. A control sample was also formed in this fashion, though instead of an alkoxysilane adduct, KANEKA OR110S-brand polyacrylate was used in the same amount. The identities and relative amounts of the various constituents are shown below in Table 1.

TABLE 1

| Resin | Description | 1(wt. %) | 2(wt. %) | 3(wt. %) | 4(wt. %) | C (wt. %) |
|---|---|---|---|---|---|---|
| 14K PBA/APTES | Experimental resin | 83.66 | — | — | — | — |
| 14K PBA/APTMS | Experimental resin | — | 83.66 | — | — | — |
| 20K Terpolymer/APTES | Experimental resin | — | — | 83.66 | — | — |
| 30K Terpolymer/APTES | Experimental resin | — | — | — | 83.66 | — |
| Kaneka OR110S | Commercial resin control | — | — | — | — | 83.66 |
| Mesamoll | Plasticizer | 6.33 | 6.33 | 6.33 | 6.33 | 6.33 |
| Cab-O-Sil TS530 | Filler | 4.19 | 4.19 | 4.19 | 4.19 | 4.19 |
| Vinyltrimethoxysilane | Crosslinker | 1.66 | 1.66 | 1.66 | 1.66 | 1.66 |
| APTMS | Crosslinker | 2.08 | 2.08 | 2.08 | 2.08 | 2.08 |
| Dibutyltin dilaurate | Catalyst | 2.08 | 2.08 | 2.08 | 2.08 | 2.08 |

Figure 3:
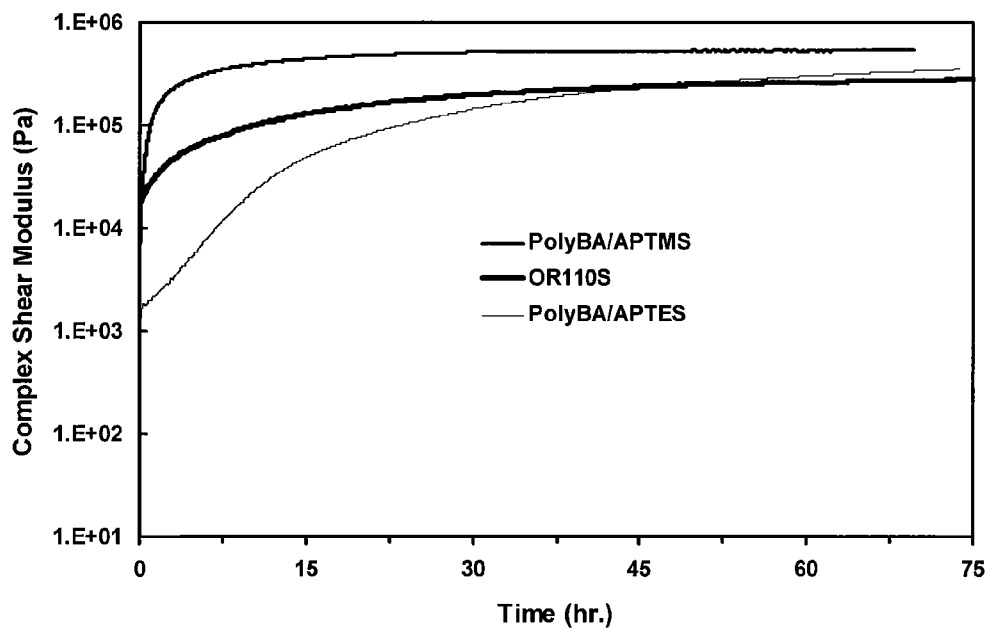
FIG. 3 shows a Rheometric analysis of each of a 13,000 Mn polybutylacrylate/APTMS- and a 13,000 Mn polybutylacrylate/APTES-containing moisture curable composition compared with Kaneka XMAP OR110S as a control.
Figure 4:
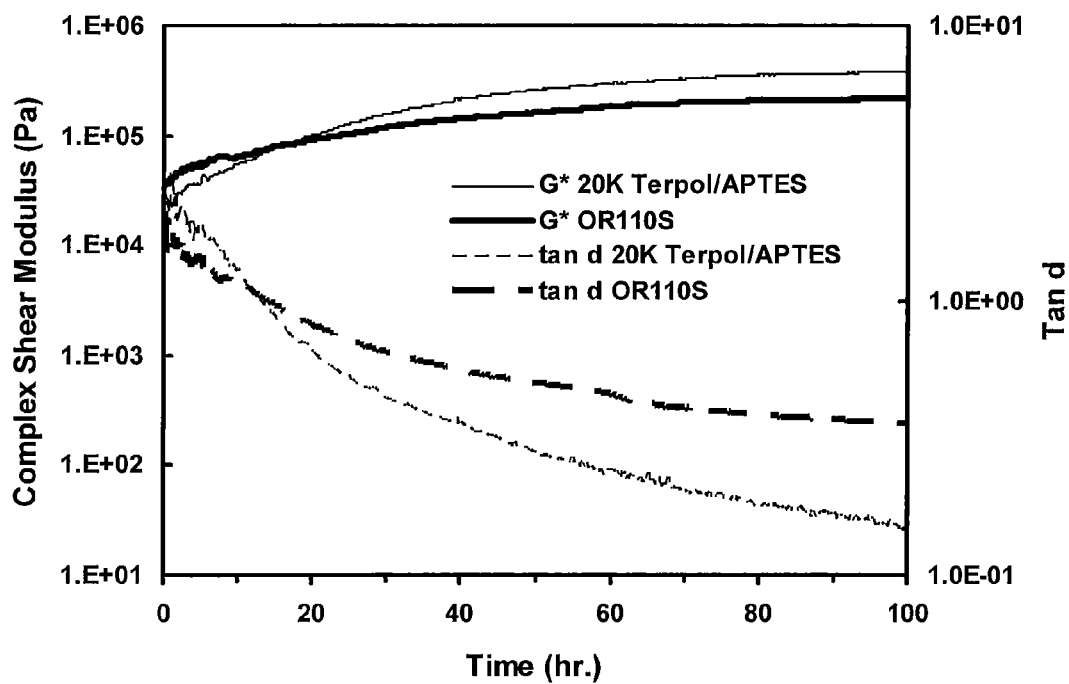
FIG. 4 shows a Rheometric analysis of a 20,000 MW butyl-ethyl-methoxyethyl acrylate (45/30/25 mole ratio) terpolymer/APTES-containing moisture curable composition with Kaneka XMAP OR110S as a control.
Figure 5:
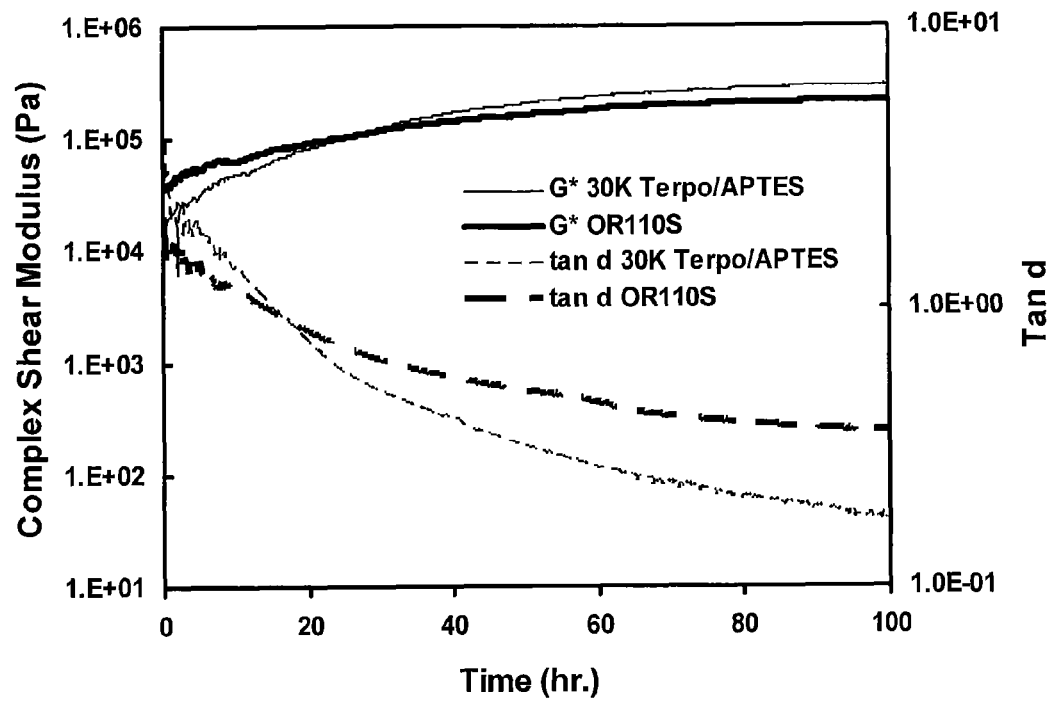
FIG. 5 shows a Rheometric analysis of a 30,000 MW butyl-ethyl-methoxyethyl acrylate (75/20/5 mole ratio) terpolymer/APTES-containing moisture curable composition with Kaneka XMAP OR110S as a control.

APTES = aminopropyltriethoxysilane
APTMS = aminopropyltrimethoxysilane
14K PBA/APTES = 14,000 MW Polybutylacrylate/APTES product
14K PBA/APTMS = 14,000 MW Polybutylacrylate/APTMS product
20K Terpolymer/APTES = 20,000 MW Butyl-ethyl-methoxyethyl acrylate terpolymer (45-30-25 mole ratio)/APTES
30K Terpolymer/APTES = 30,000 MW Butyl-ethyl-methoxyethyl acrylate terpolymer (75-20-5 mole ratio)/APTES Samples were immediately loaded onto the rheometer with 8 mm diameter parallel plates at a gap of 1.0 mm. For the oscillatory rheometer experiment, strain was set at 0.04% with a minimum torque specification of 30 microN*m. Frequency was set to 30 rad/s. One data point was collected every ten minutes over a total experiment run time of six or seven days. Complex shear modulus was plotted as a function of time to determine relative cure speed and degree of ultimate cure for the different moisture cure formulations. Reference to FIGS. 3-5 show these results.

What is claimed is:

1. A process for preparing aminoalkylalkoxysilane-functionalized hydrocarbon compounds, comprising:
Providing (a)

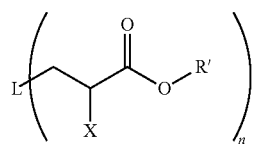

I

L is alkyl, poly(alkyl) or poly(acrylate), alkylene or poly(alkylene), alkenyl or poly(alkenyl), alkenylene or poly(alkenylene), aromatic or an aromatic ring system, X is a leaving group, R' is alkyl, and n is 1-4, or

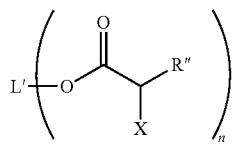

II

L is alkyl, poly(alkyl) or poly(acrylate), alkylene or poly(alkylene), alkenyl or poly(alkenyl), alkenylene or poly(alkenylene), aromatic or an aromatic ring system, X is a leaving group, R" is alkyl, and n is 1-4, (b) an aminoalkylalkoxysilane, (c) base, and (d) organic solvent in a vessel and mixing (a)-(d) for a time sufficient to form an aminoalkylalkoxysilane-functionalized hydrocarbon compound.

2. The process of claim 1, wherein X is a halogen, tosylate or mesylate.

3. The process of claim 1, wherein X is a halogen selected from chlorine, bromine or iodine.

4. The process of claim 1, the base is potassium carbonate or a trialkyl amine.

5. The process of claim 1, wherein the organic solvent is acetonitrile.

6. The process of claim 1, wherein mixing occurs at a temperature of reflux.

7. The process of claim 1, wherein mixing at reflux occurs for a period of time of about 2 to about 24 hours.

8. The process of claim 1, wherein mixing at reflux occurs for a period of time of about 2 to about 24 hours to achieve a yield of greater than about 90% of the aminoalkyl alkoxysilane-functionalized hydrocarbon compound.

9. The process of claim 1, wherein the compound shown in structure I or II is made by a controlled radical polymerization technique.

10. An aminoalkyl alkoxysilane-functionalized hydrocarbon compound made in accordance with the process of claim 1.

11. A moisture curable composition, comprising:
(a) an aminoalkyl alkoxysilane-functionalized hydrocarbon compound made in accordance with the process of claim 1; and
(b) a moisture cure calayst.

12. The composition of claim 11, further comprising one or more of a filler component, a toughening component, a plasticizer component and a cross linker component.

* * * * *

UNITED STATES PATENT AND TRADEMARK OFFICE
CERTIFICATE OF CORRECTION

| | | |
|---|---|---|
| PATENT NO. | : 8,729,179 B1 | Page 1 of 1 |
| APPLICATION NO. | : 13/738348 | |
| DATED | : May 20, 2014 | |
| INVENTOR(S) | : Philip T. Klemarczyk, Anthony F. Jacobine and Joel D. Schall | |

It is certified that error appears in the above-identified patent and that said Letters Patent is hereby corrected as shown below:

In the specification
Column 1, line 51: Change "availablity" to -- availability --.
Column 2, line 13: Change "or or" to -- or --.
Column 3, line 61: Change "simililarly" to -- similarly --.
Column 5, lines 29 and 30: Change "particlarly" to -- particularly --.
In the claims
Column 9, line 43: Before "L", insert -- wherein --.
Column 9, line 43: Change "alkyl, poly(alkyl) or poly(acrylate)," to -- alkyl or poly(alkyl), --.
Column 10, line 20: Change "L" to -- wherein L' --.
Column 10, line 20: Change "alkyl, poly(alkyl) or poly(acrylate)," to -- alkyl or poly(alkyl), --.
Column 10, line 52: Change "calayst" to -- catalyst --.

Signed and Sealed this
Fifth Day of April, 2016

Michelle K. Lee
*Director of the United States Patent and Trademark Office*